United States Patent [19]

Ueno

[11] Patent Number: 5,828,439
[45] Date of Patent: Oct. 27, 1998

[54] OPHTHALMOLOGIC DEVICE FOR MEASURING EYE REFRACTIVE POWER

[75] Inventor: Yasunori Ueno, Kawasaki, Japan

[73] Assignee: Nikon Corporation, Tokyo, Japan

[21] Appl. No.: 739,314

[22] Filed: Oct. 29, 1996

[30] Foreign Application Priority Data

Nov. 15, 1995 [JP] Japan .................................... 7-321022

[51] Int. Cl.⁶ ...................................................... A61B 3/10
[52] U.S. Cl. .......................................... 351/205; 351/211
[58] Field of Search .................................... 351/205, 210, 351/211, 221, 206; 396/18, 432

[56] References Cited

U.S. PATENT DOCUMENTS 4,390,255  6/1983  Nohda et al. ............................ 351/212
5,555,039  9/1996  Iki et al. .................................. 351/205

*Primary Examiner*—Huy Mai
*Attorney, Agent, or Firm*—Klarquist Sparkman Campbell Leigh & Whinston, LLP

[57] ABSTRACT

Ophthalmologic apparatus and methods are disclosed that permit reliable measurement of the refractive power of an eye both after and during invasive eye surgery. The refractive-power measurement is based on the output of a light sensor when a light flux, projected onto the retina, is reflected from the retina. The apparatus comprises a processor in which data regarding the intraocular pressure of the eye, before surgery and/or during surgery, can be entered. With refractive-power measurements obtained during surgery, the processor is operable to calculate, from the intraocular pressure data, a corrected refractive-power value for the subject eye under normal intraocular pressure conditions.

21 Claims, 2 Drawing Sheets

OPHTHALMOLOGIC DEVICE FOR MEASURING EYE REFRACTIVE POWER

FIELD OF THE INVENTION

This invention pertains to opto-medical devices, particularly to ophthalmologic devices for measuring the refractive power of a patient's eye.

BACKGROUND OF THE INVENTION

The eye is a delicate and precise optical system. Whenever any of various symptoms arise in an eye, an appropriate treatment or surgery is implemented in order to restore the eye's function. Whenever eye surgery aimed at restoring eye function is considered, concern is also directed to restoring, if necessary, eye shape and refractive power. Whether a surgery on the eye was successful or not is often determined by evaluating the degree to which normal eye refractive power is restored.

In recent years as the population has aged, the proportion of surgeries, performed on the front of the eye, represented by cataract surgery has increased. Such surgery usually involves the implantation of a replacement lens (intraocular lens) in the eye, which can result in postoperative changes in corneal shape and in the refractive power of the eye. During and after such surgeries, the ability to measure and monitor the refractive power of the eye and corneal shape of the eye is of critical importance in determining the success of the surgery.

During cataract surgery and other such invasive procedures, the intraocular pressure in the subject eye can change significantly, including drop to sub-normal levels. Such a change in pressure can affect the refractive power of the eye. Ophthalmic surgeons frequently need to measure the eye refractive power during surgery. If the refractive power of the eye is measured during surgery when intraocular pressure is decreased, the measured value will likely be substantially different than if the measurement had been performed on an intact eye.

Conventional ophthalmologic measuring devices are incapable of accounting for such changes in pressure and thus are unreliable in providing a refractive-power measurement during surgery that can be confidently regarded as accurately representing the actual refractive condition of the intact eye.

In view of the foregoing, there is a need for apparatus and methods for measuring the refractive power of the eye, even during surgery when intraocular pressure in the eye is decreased, in order to obtain a measurement that accurately indicates the actual refractive condition of the eye, including the refractive condition expected after completion of surgery. Such measurements are crucial in evaluating the expected and actual recovery process.

SUMMARY OF THE INVENTION

The shortcomings of the prior art as summarized above are solved by the present invention that provides apparatus for measuring the refractive power of a subject eye. Such an apparatus comprises a refractive-power measurement subsystem. The refractive-power measurement subsystem comprises (1) a first light source operable to project a light flux along a first optical axis onto the retina of a subject eye having a first intraocular pressure condition; and (2) a light sensor situated relative to the eye and the light source to receive the light flux that reflects from the retina. The light sensor is operable to generate, from the received light flux, a refractive-power measurement signal for the subject eye at the first intraocular pressure condition. The apparatus also comprises a processor connected to the light sensor so as to receive from the light sensor the refractive-power measurement signal corresponding to the first intraocular pressure condition. The processor is operable to calculate, from such a signal and previously entered data concerning a second intraocular pressure condition for the subject eye, a "corrected" refractive-power value for the subject eye under the second intraocular pressure condition. The corrected value is displayed.

By way of example, the first intraocular pressure condition is an intraocular pressure condition in the eye during invasive surgery of the eye; and the second intraocular pressure condition is an intraocular pressure condition in the same eye under normal intact conditions.

The refractive-power measurement subsystem further preferably comprises a chopper situated between the first light source and the eye; an image rotator situated between the chopper and the eye; an objective lens situated between the eye and the light sensor; and a first aperture stop, defining a slit-shaped aperture, situated between the objective lens and the light sensor.

The apparatus also preferably comprises a "fogging" subsystem. Such a subsystem comprises a (visible) second light source, a visual target situated between he second light source and the eye, a first projection lens situated between the target and the eye, an aperture stop (defining an aperture) situated between the first projection lens and the eye, and a second projection lens situated between the aperture stop and the eye.

Further preferably, the apparatus comprises first and second phototransducers, a processor, and electronic circuitry operable to receive signals from the first and second phototransducers and process the signals to outputs conducted to the processor. The processor is also operable to calculate a corrected refractive-power value from a difference of the second intraocular pressure condition from the first intraocular pressure condition.

The foregoing features and advantages, as well as other features and advantages, of the present invention will be apparent from the following drawings and detailed description.

DETAILED DESCRIPTION

The present invention provides apparatus that are operable to accurately measure the refractive power of the eye. Such measurements can be performed reliably at any time, including during invasive eye surgery. Furthermore, the apparatus is operable to adjust the measured value of refractive-power value by a "pressure factor" (reflective of a difference in ocular pressure of a first intraocular pressure condition of the eye relative to a second intraocular pressure condition) and thus provide a "corrected" refractive-power value.

The pressure factor represents any change in intraocular pressure of the eye that may have occurred, for example, during eye surgery relative to the intraocular pressure of the same eye during normal conditions. The pressure factor can be an estimated difference of intraocular pressure of the eye during surgery relative to the intraocular pressure of the intact eye, such as before beginning the surgery. Such a pressure factor is determined from actual pressure measurements made of the eye both before onset of eye surgery and actually during the surgery. Pressure data used by the apparatus for determining the pressure factor can be entered into and stored in an electronic memory in the apparatus for later use by the apparatus in calculating the corrected refractive-power value.

As described in detail below, the measured refractive power of the eye is determined from a measured output of a light sensor receiving a light flux that is projected onto and reflected from the retina.

The corrected refractive-power value is preferably displayed by the apparatus. The apparatus also preferably displays the value of the intraocular pressure in the eye. The display can be a CRT, liquid-crystal display, LED alphanumeric display, or any of various other displays.

Thus, an apparatus according to the present invention permits one to measure the refractive power of the subject eye that would exist under normal conditions, event though the measurement is actually performed during or immediately after surgery, thus improving the reliability with which the measured value indicates the actual refractive power of an intact eye (i.e., an eye before surgery or after recovery from surgery).

An apparatus according to the present invention comprises a refractive-power measuring subsystem (also termed herein a "first optical subsystem") and optionally a fogging subsystem (also termed herein a "second optical subsystem"). The measurement principle of the refractive-power measuring subsystem is based on the retinoscopy method, wherein the refractive power is measured by detecting the rate of movement of a shadow inside the pupil. Details on the retinoscopy method are set forth in U.S. Pat. No. 4,390,255 to Nohda et al., incorporated herein by reference. Reference is also made to Japan Laid-Open Patent Document No. SHO 55-86437.

Figure 1:
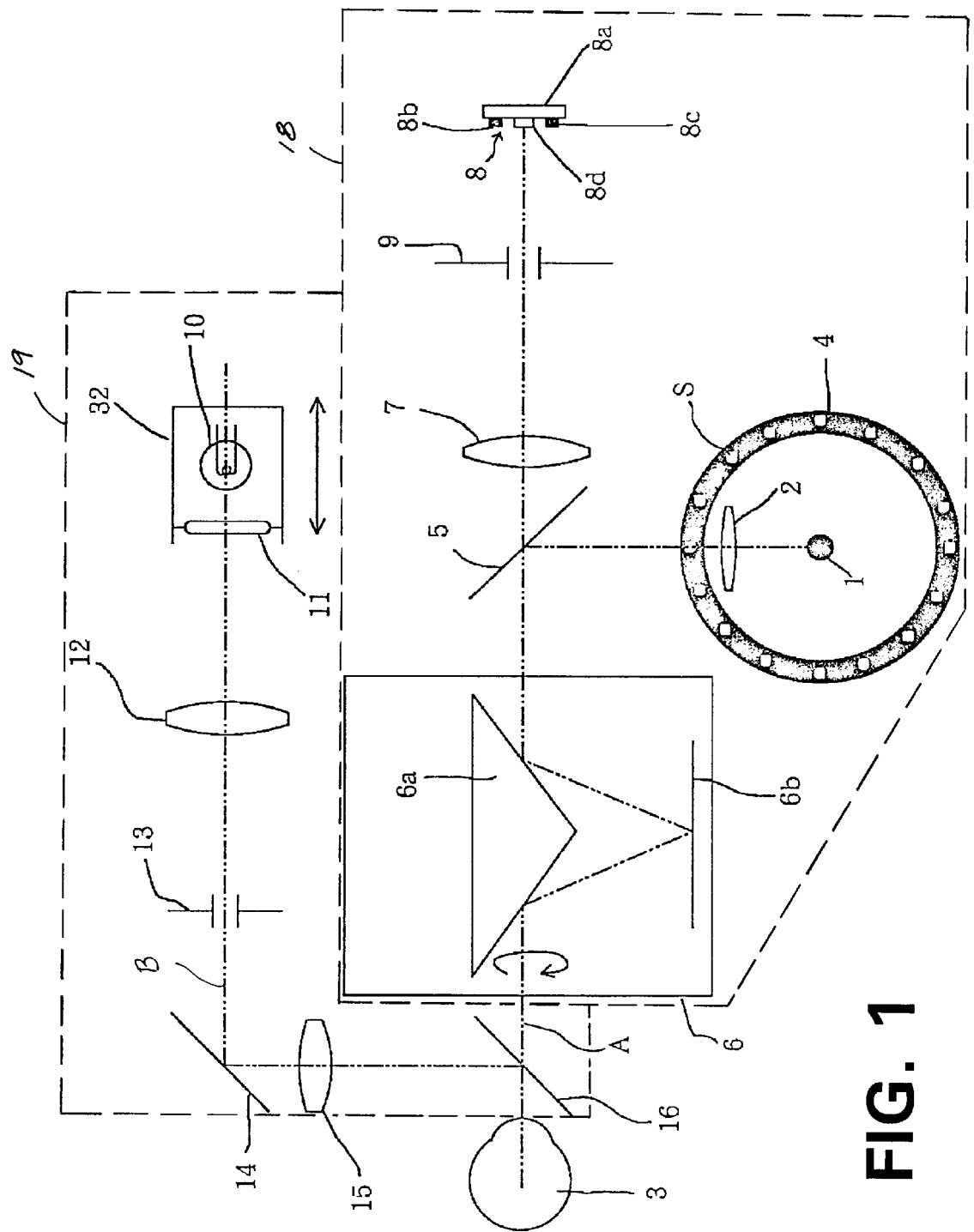
FIG. 1 schematically depicts the optical configuration of a preferred embodiment of an apparatus according to the present invention.

FIG. 1 schematically depicts an example embodiment of this invention. The FIG. -1 embodiment comprises a refractive-power measuring subsystem 18 for measuring refractive power of an eye. The refractive-power measuring subsystem 18 comprises a light source 1 (preferably an infrared light source), a condenser lens 2, a chopper 4, a half-mirror 5, an image rotation system 6, an objective lens 7, a light receptor 8, and an aperture stop 9. Each of these components is discussed below.

The light source 1 is preferably a light-emitting diode (LED). A flux of infrared light from the light source 1 is focused on the pupil of the subject eye 3 by a condenser lens 2. The infrared light flux is chopped. A preferred chopper 4, shown in FIG. 1, comprises a rotatable hollow cylinder (axially extending orthogonally to the plane of the page) in which the infrared light source 1 and condenser lens 2 are situated. The chopper 4 has multiple slit-shaped openings S formed around the circumference of the cylinder and extending perpendicularly to the plane of FIG. 1.

The chopper 4 is rotated about an axis perpendicular to the plane of FIG. 1 by a drive system (not shown) such as an electric motor. The rotation is very rapid to achieve an extremely rapid chop rate. The light flux passing through the slit-shaped openings S has a linear profile. The chopped light flux impinges on a half-mirror 5 that reflects the linear light flux along an axis A toward the subject eye 3.

The linear light flux reflected from the half-mirror 5 enters an image rotator 6 comprising a prism 6a and a mirror 6b. Rotation of the rotator 6 about the axis A causes a corresponding rotation of the orientation of the line of light flux about the axis A. During a measurement, the rotator 6 rotates at a constant high velocity.

Thus, an image of the light source 1 is formed at the pupil of the subject eye 3 such that the retina of the eye 3 is scanned by the rotating linear light flux accompanying the rotation of the chopper 4.

Infrared light reflected from the retina of the subject eye 3 returns through the image rotator 6 and the half-mirror 5. The light then passes through an objective lens 7 and an aperture stop 9 and impinges on a light receptor 8. The aperture stop 9 defines a slit-shaped opening with a longitudinal dimension extending orthogonally to the plane of the page; the opening is situated substantially at the focal point of the objective lens 7.

The light receptor 8 comprises a substrate 8a, and photoelectric transducers 8b, 8c and a quartered photoelectric transducer 8d mounted on the substrate 8a. The photoelectric transducers 8b, 8c are used in the measurement of refractive power and are arranged along a line corresponding with the scanning direction of the light flux on the subject eye 3.

Figure 2:
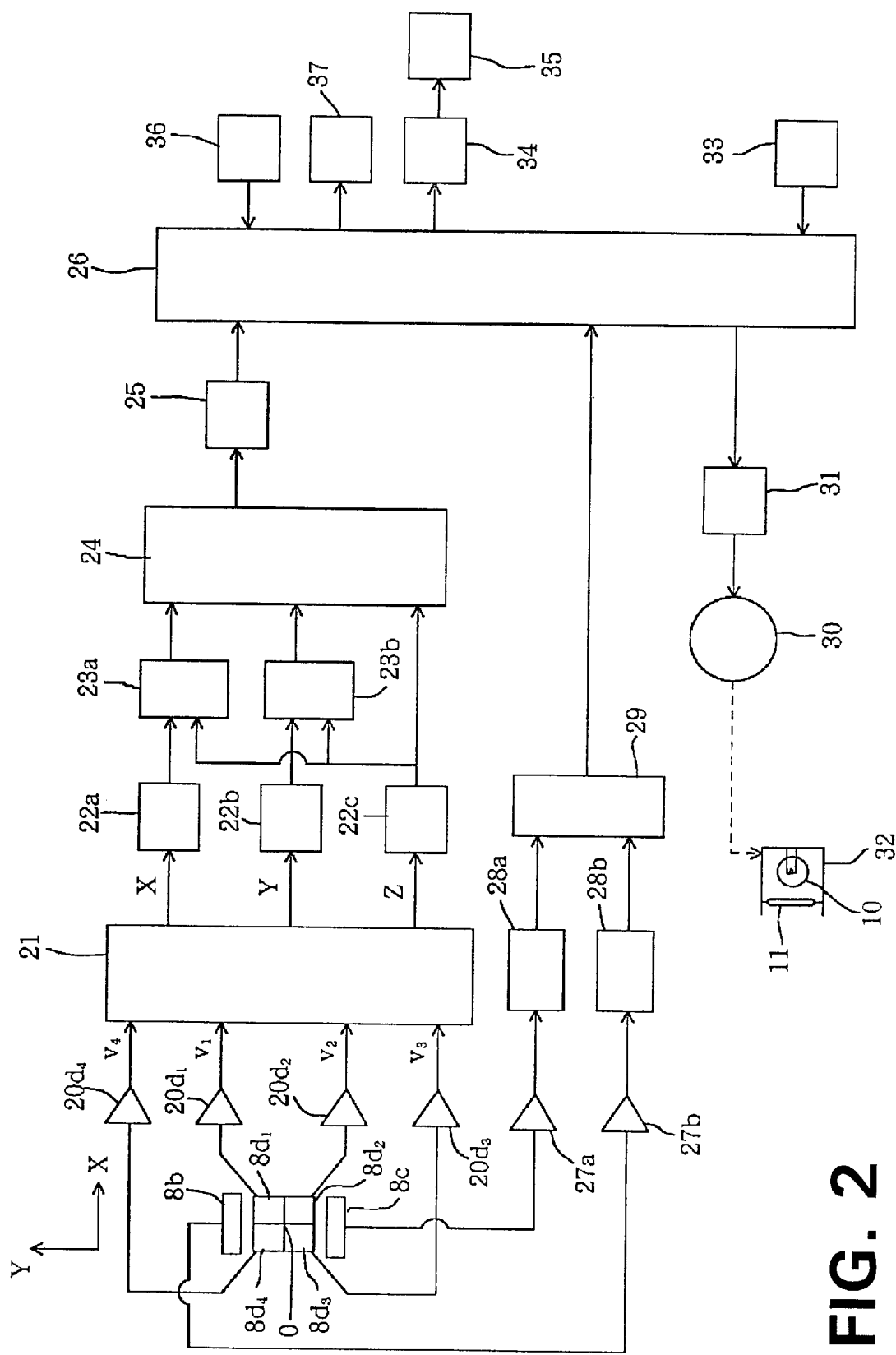
FIG. 2 is a block diagram of the manner in which electrical signals are processed by the example embodiment of FIG. 1 so as to produce a measurement of the refractive power of a subject eye.

The quartered photoelectric transducer 8d, situated between the photoelectric transducers 8b, 8c, actually comprises four transducer elements $8d_1$ through $8d_4$, which are arranged as shown in FIG. 2 (showing the light receptor 8 as viewed along the optical axis A). The center O of the four transducer elements $8d_1$–$8d_4$ is aligned with the optical axis A. I.e., the four transducer elements $8d_1$–$8d_4$ receive the reflected light from the cornea and are thus used to horizontally and vertically align the light axis A with the subject eye.

The FIG.-1 embodiment also comprises a fogging subsystem 19. To obtain a measurement using such a subsystem, light from a visual target is directed into the eye and is intentionally defocused by moving it outside the accommodation range of the eye. (This is termed "fogging" because the image of the visual target is blurred.) The fogging subsystem comprises a visible light source 10, a visual target 11, a housing 32, a projection lens 12, an aperture stop 13, a mirror 14, a lens 15, and a dichroic mirror 16. The dichroic mirror 16 transmits infrared light and reflects visible light.

The visible light source 10 generates a flux of visible light to illuminate the visual target 11. The visual target 11 and the visible light source 10 are mounted together in a housing 32 to form a single unit. The visual target 11 is preferably a "star burst" pattern. The housing 32 is operable to move back and forth along the optical axis B (as indicated by the arrows 17) as urged by a stepping motor or the like engaged with the housing, as explained below.

Light transmitted through the visual target 11 passes through the projection lens 12 and an aperture defined by the aperture stop 13. The visible light then reflects from a mirror 14, passes through a lens 15, and reflects from the dichroic mirror 16 toward the eye 3 for projection onto the retina of the eye 3 by the lens of the subject eye 3. Thus, an image of the visual target 11 is formed on the retina of the subject eye 3. Although the lens 15 is normally not adjustable on the axis B, the lens 15 is operable to position the aperture 13 at a location on the axis B that is conjugate with the pupil of the subject eye 3. In other words, the lens 15 enables a constant pupil size to be maintained even if the subject eye 3 changes.

If the refractive characteristic of the subject eye 3 remains constant, the position of the image of the visual target 11 that is formed on the retina of the subject eye 3 remains at a specific location on the optical axis B. In other words, the visual target 11 is situated on the optical axis B at a location having a direct correlation with the refractive power of the subject eye 3.

Whenever the eyeball is anesthetized during surgery on the eye, it is not necessary to use the fogging subsystem for eliminating accommodation. This is because an anaesthetized eye has no accommodation ability.

FIG. 2 schematically illustrates a preferred configuration of the electrical processing system of the FIG.-1 embodiment.

Photoelectric current generated in each of the four transducer elements $8d_1$–$8d_4$ upon exposure to light (reflected from the cornea of the subject eye) is converted to low-impedance electrical signals in corresponding amplifiers $20d_1$–$20d_4$, respectively. Voltage signals produced by the amplifiers $20d_1$–$20d_4$ are input to an adder-subtractor 21. From the output of the four transducer elements $8d_1$–$8d_4$, the adder-subtractor 21 outputs an "X" signal corresponding to a particular positional movement in the X direction of cornea-reflected light, a "Y" signal corresponding to a particular positional movement in the Y direction of cornea-reflected light, and a sum signal "Z" indicating the intensity of the cornea-reflected light. The X and Y directions are in a plane perpendicular to the measurement optical axis A.

Considering that the output from the amplifiers $20d_1$–$20d_4$ is $v_1$–$v_4$, respectively, the X signal is $(V_1+V_2)-(V_3+v_4)$, and the Y signal is $(v_1+v_4)-(v_3+v_3)$. The X, Y, and Z output signals from the adder-subtractor 21 are converted using low-band filters $22a$–$22c$, respectively, into direct-current voltages in which the chopping frequency component is suppressed. Analog dividers $23a$, $23b$ respectively normalize the X and Y coordinate signals to prevent the respective coordinate signal from changing due to differences in the refractive index of the cornea.

The normalized X and Y coordinate signals and the sum signal Z are continuously extracted, in an alternating manner, by an analog switch 24. The extracted signals are converted to digital signals by an analog-to-digital (AD) converter 25, and then input to a processor 26. The processor 26 drives a display circuit 37 which displays the digitized X and Y coordinate signals.

Measurement of refractive power is accomplished by measuring the phase difference between the signal output of each of the two photoelectric transducers $8b$, $8c$ (which receive light reflected from the retina of the subject eye). If the eye is emmetropic during scanning of the retina by the chopped light flux exiting the chopper 4, the position of the opening defined by the aperture stop 9 corresponds exactly with the neutral point. Since the light flux propagating from the opening defined by the aperture stop 9 toward the light receptor is similarly light and then dark, the phases of the output signals from the two photoelectric transducers $8b$, $8c$ will be equal.

Whenever the subject eye 3 is not emmetropic, light and dark stripes corresponding with any of various refractive errors of the eye will exit from the opening defined by the aperture stop 9. As a result, the phases of the output signals of the photoelectric transducers $8b$, $8c$ will differ according to the refractive errors of the subject eye 3. The refractive power of the subject eye 3 can be determined from the phase difference in the output signals of the photoelectric transducers $8b$, $8c$.

As discussed above, the intraocular pressure in the subject eye 3 will typically be subnormal during invasive eye surgery. Consequently, measurement of the refractive power of the eye under such conditions will typically yield an abnormal value. To convert such an abnormal reading to a refractive-power value indicative of the same eye during normal conditions or after the eye has healed from the surgery, the measured intraocular pressure of the eye during surgery, or the difference between the value of the intraocular pressure under normal conditions and the value of the intraocular pressure during surgery, is entered into the apparatus ahead of time; and the refractive-power value obtained during surgery is corrected based on this intraocular pressure information, as described below.

First, referring further to FIG. 2, data concerning the intraocular pressure of the eye are entered, in advance, into the computer 26 via an input unit 36. Such intraocular-pressure data, as discussed above, comprise the value of the intraocular pressure during surgery, or the difference between the value of the intraocular pressure under normal conditions and the value of the intraocular pressure during surgery. Whenever the refractive power of the subject eye will not be measured during surgery, there is no need to enter such intraocular pressure data.

The outputs from the two photoelectric transducers $8b$, $8c$, after passing through respective buffers $27b$, $27a$, are shaped into square waveforms by waveform-shaper circuits $28b$, $28a$. The outputs from the waveform-shaper circuits $28b$, $28a$ are converted using a phase-difference counter 29 into a pulse number that corresponds with the phase difference. The pulse number is input to the processor 26. In the processor 26, signals are alternately input from the A–D converter 25 and the phase-difference counter 29.

When the X signal and the Y signal each indicate respective levels of nearly zero, and the sum signal Z is greater than the desired level (this is the alignment signal, i.e., when performing alignment between the subject eye and the apparatus, a desired pulse corresponding with the digital signal output by the phase-difference counter 29 is output as a drive signal to the drive circuit 31 of the stepping motor 30.) The sum signal Z is considered here because nearly zero levels can be indicated in the X signal and the Y signal even when there is a substantial positional shift between the subject eye and the apparatus.

The stepping motor 30 drives the housing 32, holding the visible light source 10 and the visual target 11. As described above, there is a one-to-one correlation between the refractive power of the subject eye 3 and the position of the visual target 11 whose image is formed on the retina of the subject eye 3. In order to relax the subject eye 3, it is necessary to focus the image of the visual target at a point slightly in front of the retina so that the subject eye 3 is directed to a remote point. The position of the housing 32, i.e., the position of the visual target 11, is set according to the signal that corresponds with the refractive power of the subject eye 3 (in this example embodiment, according to the signal that corresponds with the phase difference in the output signals from the photoelectric conversion elements $8b$, $8c$).

During use, the operator of the apparatus, after confirming that there is no positional shift between the subject eye and the apparatus itself, and that none of the subject's eyelashes or the like are in the measurement light path, turns the measurement start switch 33 ON and enters a measurement start signal into the processor 26. When the measurement start signal is entered, the processor activates the automatic fogging subsystem (as discussed above, the fogging subsystem does not necessarily have to be activated during surgery). Once any fluctuations in the output from the phase-difference counter 29 are minimized and the feedback system is in a stable state, the processor 26 receives an output signal from the phase-difference counter 29 and converts it into a frequency.

Next, the processor 26 corrects the refractive power measured under conditions of decreased eye pressure during surgery, based on the intraocular-pressure data for the subject eye that were previously entered, thus yielding a refractive power that corresponds with the normal intraocular pressure conditions. In the preferred embodiment, the corrected refractive power is entered into a CRT controller 34 of a CRT monitor 35. Thus, the refractive power of the subject eye which corresponds with normal intraocular pressure conditions is displayed on the CRT monitor 35 even during surgery.

Generally, the fogging subsystem directs the subject eye to its "far point" (an eye is able to focus on an object by accommodating from its far point to its "near point"), and the refractive-power measuring subsystem measures the accommodation state of the eye. The refractive-power measuring subsystem continuously measures in one flux plane, and the measured values are constantly fed back to the fogging subsystem, whereby the fogging subsystem moves the visual target slightly more toward the far point than the refractive condition of the eye, thereby working to "cancel" the eye's ability to accommodate. When the accommodation state of the eye thus reaches a constant value, and it is believed that the accommodation state of the eye has been sufficiently cancelled, the rotator 6 begins rotating to allow such measurements to be obtained in substantially all flux planes. When astigmatism is first detected, the measurements are complete.

Therefore, the example embodiment described above provides a measurement of the refractive power of a subject eye that corresponds with normal intraocular pressure conditions after surgery and even during surgery, thereby improving the reliability of the measured value.

In addition, because an apparatus according to the present invention can record refractive-power data, changes in this parameter during surgery and afterward can be recorded for a particular eye. With the example embodiment, it is preferred that both the refractive power and the intraocular-pressure data for the subject eye be displayed at the same time.

Additionally, the example embodiment employed the retinoscopy method as the measurement principle for the refractive-power measuring subsystem. However, the retinoscopy method is only one of several possible measurement principles that can be employed. The present invention is not limited to the retinoscopy method, and can utilize other measurement principles.

Furthermore, because the ophthalmologic apparatus according to the present invention can be used during surgery, it is preferred that the apparatus be configured as a hand-held device or as an apparatus that can be incorporated into a surgical microscope.

An apparatus according to the present invention can be used not only during surgery, but also under normal circumstances. Consequently, it is preferred that the apparatus be equipped with a means for selecting whether or not to correct the measured refractive-power value for the subject eye.

During the measurement of refractive power during surgery, the ophthalmologic apparatus of this invention corrects the measured value based on intraocular pressure data for the subject eye. Consequently, it is possible to measure the refractive power of the subject eye corresponding with the intraocular pressure under normal conditions both after surgery and during surgery, thus improving the reliability of the measured value.

Intraocular pressure can be measured using a separate instrument. Alternatively, an intraocular-pressure gauge can be incorporated into the apparatus according to the present invention. Entry of intraocular pressure data can be done using, for example, a keyboard or the like, or can be done directly from the intraocular-pressure gauge.

While the invention has been described in connection with preferred embodiments, it will be understood that it is not limited to those embodiments. On the contrary, the invention is intended to cover all alternatives, modifications, and equivalents as may be included within the spirit and scope of the invention as defined by the appended claims.

What is claimed is:

1. An apparatus for measuring the refractive power of a subject eye, the apparatus comprising:

(a) a refractive-power measurement subsystem comprising a first light source operable to project a light flux along a first optical axis onto the retina of a subject eye having a first intraocular pressure condition; and a light sensor situated relative to the eye and the first light source to receive the light flux that reflects from the retina, the light sensor being operable to generate, from the received light flux, a refractive-power measurement signal for the subject eye at the first intraocular pressure condition; and (b) a processor connected to the light sensor so as to receive from the light sensor the refractive-power measurement signal corresponding to the first intraocular pressure condition, the processor being operable to calculate, from the refractive-power measurement signal and previously entered data concerning a second intraocular pressure condition for the subject eye, and display a corrected refractive-power value for the subject eye under the second intraocular pressure condition.

2. The apparatus of claim 1, wherein the first light source generates infrared light.

3. The apparatus of claim 2, wherein the first light source is an LED.

4. The apparatus of claim 1, wherein the refractive-power measurement subsystem further comprises a chopper situated between the first light source and the subject eye, the chopper being operable to chop the light flux from the first light source and provide the light flux with a planar profile.

5. The apparatus of claim 4, wherein the refractive-power measurement subsystem further comprises an image rotator axially situated between the chopper and the subject eye, the image rotator being operable to axially rotate the planar profile of the light flux.

6. The apparatus of claim 5, wherein the refractive-power measurement subsystem further comprises an objective lens axially situated between the subject eye and light sensor.

7. The apparatus of claim 6, wherein the refractive-power measurement subsystem further comprises a first aperture stop axially situated between the objective lens and the light sensor substantially at the focal point of the objective lens, the first aperture stop defining a slit-shaped opening for passage of light from the subject eye to the light sensor.

8. The apparatus of claim 7, wherein the light sensor comprises a first photoelectric transducer, a second photoelectric transducer, and a quartered photoelectric transducer having a center situated on the optical axis.

9. The apparatus of claim 8, wherein the first and second photoelectric transducers are operable to differentially measure phase differences in the light flux reflected from the retina of the subject eye.

10. The apparatus of claim 1, further comprising a fogging subsystem operable for eliminating accommodation of the subject eye.

11. The apparatus of claim 10, wherein the fogging subsystem comprises, along a second optical axis:
   (a) a second light source operable to produce a visible light flux;
   (b) a visual target situated between the second light source and the subject eye;
   (c) a first projection lens situated between the visual target and the subject eye;
   (d) a second aperture stop defining an aperture and situated between the first projection lens and the subject eye; and
   (e) a second projection lens situated between the second aperture stop and the subject eye.

12. The apparatus of claim 11, wherein the light sensor comprises a first photoelectric transducer, and a second photoelectric transducer, the first and second photoelectric transducers being operable to differentially measure phase differences in the light flux reflected from the retina of the subject eye.

13. The apparatus of claim 1 wherein the second light source and the visual target are enclosed in a housing to maintain a fixed axial distance between the second light source and the visual target.

14. The apparatus of claim 13, further comprising a motor operably engaged with the housing to adjust the axial position of the housing on the second optical axis.

15. The apparatus of claim 14, further comprising electronic circuitry operable to receive signals from the first and second photoelectric transducers and process the signals to outputs conducted to the processor, the outputs containing information about phase differences of light as sensed by the first and second photoelectric transducers, the phase differences corresponding to the refractive power of the subject eye, the processor actuating the motor to adjust the axial position of the housing to compensate for any positional shift of the subject eye relative to the apparatus.

16. The apparatus of claim 1, wherein the first intraocular pressure condition is a fluid pressure condition in the subject eye during invasive surgery of the subject eye, and the second intraocular pressure condition is an intraocular pressure condition in the intact subject eye.

17. The apparatus of claim 16, wherein the processor is operable to calculate the corrected refractive-power value from a difference of the second intraocular pressure condition from the first intraocular pressure condition.

18. The apparatus of claim 1, further comprising a display operable to display the refractive-power value and intraocular pressure data of the subject eye.

19. The apparatus of claim 1, further comprising a switch operable to select whether or not the processor determines a refractive-power value of the subject eye under the current intraocular pressure condition of the eye or a corrected refractive-power value.

20. In a method for measuring the refractive power of a subject eye during invasive surgery, an improvement, comprising:
   (a) before the onset of the surgery, measuring a pre-surgery intraocular pressure for the subject eye;
   (b) storing data concerning the pre-surgery intraocular pressure in a memory;
   (c) after onset of the invasive surgery, measuring an intraocular pressure for the subject eye, and measuring the refractive power of the subject eye; and
   (d) from the data obtained in steps (b) and (c), calculating a corrected intraocular pressure of the subject eye under a normal condition.

21. An apparatus for measuring the refractive power of a subject eye, the apparatus comprising:
   (a) a refractive-power measurement subsystem comprising a light source operable to project a light flux along a first optical axis onto the retina of a subject eye having a first intraocular pressure condition; and a light sensor situated relative to the eye and the light source to receive the light flux that reflects from the retina, the light sensor being operable to generate, from the received light flux, a refractive-power measurement signal for the subject eye at the first intraocular pressure condition;
   (b) a processor connected to the light sensor so as to receive from the light sensor the refractive-power measurement signal corresponding to the first intraocular pressure condition, the processor being operable to calculate, from the refractive-power measurement signal and previously entered data concerning a second intraocular pressure condition for the subject eye a corrected refractive-power value for the subject eye under the second intraocular pressure condition, the corrected refractive-power value being calculated from a difference of the refractive-power value under the second intraocular pressure condition from the refractive-power value under the first intraocular pressure condition; and
   (c) a display connected to the processor and operable to display the corrected refractive-power value.

* * * * *

UNITED STATES PATENT AND TRADEMARK OFFICE
CERTIFICATE OF CORRECTION

PATENT NO. : 5,828,439

DATED : October 27, 1998

INVENTOR(S) :
YASUNORI UENO

It is certified that error appears in the above-indentified patent and that said Letters Patent is hereby corrected as shown below:

Column 2, line 27, "he" should be --the--.

Column 3, line 23, "event" should be --even--.

Column 5, line 17, "20d$_1$-20d$_4$" should be --20d$_1$-20d$_4$--.

Column 5, lines 28 and 29, "$(V_1 + V_2) - (V_3 + V_4)$" should be
--$(v_1 + v_2) - (v_3 + v_4)$--.

Column 5, line 30, "$(v_1 + v_4) - (v_3 + v_3)$" should be --$(v_1 + v_4) - (v_2 + v_3)$--.

In the Claims:

Column 9, line 26, claim 13, "claim 1" should be --claim 12--.

Column 10, line 40, claim 21, insert a comma --,-- after "eye" and before "a".

Signed and Sealed this

Nineteenth Day of October, 1999

Attest:

Attesting Officer

Q. TODD DICKINSON

Acting Commissioner of Patents and Trademarks